United States Patent
Zhang

(10) Patent No.: US 8,650,932 B2
(45) Date of Patent: Feb. 18, 2014

(54) SENSOR SYSTEM WITH CLOSE-LOOP-ADSORPTION CIRCULATION

(75) Inventor: Shou-Hua Zhang, Arcadia, CA (US)

(73) Assignee: Smiths Detection Inc., Germantown, MD (US)

( * ) Notice: Subject to any disclaimer, the term of this patent is extended or adjusted under 35 U.S.C. 154(b) by 221 days.

(21) Appl. No.: 13/122,997

(22) PCT Filed: Oct. 15, 2009

(86) PCT No.: PCT/US2009/060855
§ 371 (c)(1),
(2), (4) Date: Jun. 1, 2011

(87) PCT Pub. No.: WO2010/045467
PCT Pub. Date: Apr. 22, 2010

(65) Prior Publication Data
US 2011/0247396 A1    Oct. 13, 2011

Related U.S. Application Data

(60) Provisional application No. 61/106,314, filed on Oct. 17, 2008.

(51) Int. Cl.
*G01N 33/00* (2006.01)
(52) U.S. Cl.
USPC ........... 73/23.2; 73/23.34; 73/31.05; 73/1.02; 73/1.03; 73/1.04
(58) Field of Classification Search
USPC .............. 73/23.2, 31.01, 31.02, 31.05, 31.07, 73/1.02–1.07, 23.34
See application file for complete search history.

(56) References Cited

U.S. PATENT DOCUMENTS

| | | | | |
|---|---|---|---|---|
| 3,958,938 A | * | 5/1976 | Doonan et al. | 435/30 |
| 4,056,967 A | * | 11/1977 | Roberts | 73/864.81 |
| 5,496,733 A | * | 3/1996 | Spandau et al. | 436/52 |
| 6,042,788 A | * | 3/2000 | De Wit et al. | 422/82.02 |
| 7,052,468 B2 | * | 5/2006 | Melker et al. | 600/532 |
| 2001/0027678 A1 | * | 10/2001 | Mottram et al. | 73/23.2 |
| 2004/0110299 A1 | * | 6/2004 | Sivavec | 436/25 |
| 2007/0062255 A1 | * | 3/2007 | Talton | 73/23.3 |

OTHER PUBLICATIONS

International Search Report for PCT/US2009/060855, issued Feb. 18, 2010, 4 pages.

* cited by examiner

*Primary Examiner* — Hezrone E Williams
*Assistant Examiner* — Alexander Mercado
(74) *Attorney, Agent, or Firm* — Foley and Lardner LLP

(57) ABSTRACT

A detection and identification system includes a sensor unit (100) having a sensor array that detects and identifies at least one chemical included in an air flow. The system also includes a pump (120) that drives the air flow through the detection and identification system, in which the pump receives the air flow that has passed out of the sensor unit. The system further includes an adsorption unit (130) that dries and cleans the air flow within the detection and identification system, to obtain a substantially dry and clean air flow, in which the adsorption unit receives the air flow that has passed out of the pump. The system also includes at least one valve (140) that receives the substantially dry and clean air flow that has passed through the adsorption unit. The valve provides the substantially dry and clean air flow to the sensor unit in a close-loop circulation operation to thereby clean a sensor array. The system receives input air from an external environment and then to the sensor unit, and provides exhaust air out to the external environment, in an open-loop flow operation of the detection and identification system in which the input air sample is analyzed and identified.

16 Claims, 2 Drawing Sheets

SENSOR SYSTEM WITH CLOSE-LOOP-ADSORPTION CIRCULATION

This application claims benefit to U.S. provisional patent application no. 61/106,314, filed Oct. 17, 2008 to Zhang, which is hereby incorporated by reference in its entirety.

BACKGROUND

Sensor units having one or more sensors for detecting different types of threats are becoming very useful in today's society, with applications in air, water, beverage, and food contamination. In more detail, chemical and biological warfare pose both physical and psychological threats to military and civilian forces, as well as to civilian populations, while air, water, beverage and food contaminations pose threats to people's daily life.

Sensor arrays exist, such as the ENOSE® sensor unit, also referred to as Cyrano 320, a handheld sensor unit manufactured by Smiths Detection, Inc. However, there is a need to provide sensor arrays with improved performance characteristics.

SUMMARY

In accordance with one embodiment, there is provided a detection and identification system that includes a sensor unit having a sensor array that detects and identifies at least one chemical included in an air flow, the sensor unit including a sensor array. The system also includes a pump that drives the air flow through the detection and identification system, in which the pump receives the air flow that has passed out of the sensor unit. The system further includes an adsorption unit that dries and cleans the air flow within the detection and identification system, to obtain a substantially dry and substantially clean air flow, in which the adsorption unit receives the air flow that has passed out of the pump. The system also can include at least one valve that receives the substantially dry and clean air flow that has passed through the adsorption unit. The at least one valve can provide the substantially dry and clean air flow to the sensor unit in a close-loop circulation operation to thereby purge and clean the sensor array. The system also operates to receive an air sample from an external environment and can exhaust excess air to the external environment in an open-loop flow operation.

In accordance with another embodiment, there is provided a detection and identification method for a sensor system having a sensor array that detects and identifies at least one chemical included in an air flow, the sensor system including a sensor array. Air flow is moved through the sensor system by way of, for example, a pump. The air flow is dried and cleaned by an adsorption unit that receives the air flow that has passed out of the pump, to obtain a substantially dry and substantially clean air flow. The substantially dry and clean air flow that has passed through the adsorption unit is received by at least one valve. The at least one valve provides the substantially dry and clean air flow to the sensor array in a close-loop circulation operation to thereby purge and clean the sensor array. The system also can operate to receive input air sample from an external environment and provide exhaust air out to the external environment in an open-loop flow operation.

In accordance with yet another embodiment, there is provided a computer readable medium embodying computer program product for detecting and identifying chemicals or contaminants in an air sample for a sensor system. The computer program product, when executed by a computer or a microprocessor, drives the computer or the microprocessor to perform a steps of pumping air flow through the sensor system by way of a pump; drying and cleaning the air flow that has passed out of the pump, to obtain a substantially dry and substantially clean air flow; and receiving the substantially dry and clean air flow by at least one valve. The substantially dry and clean air flow is provided by the at least one valve to the sensor system in a close-loop circulating operation to thereby clean a sensor array of the sensor system. The at least one valve receives an input air sample from an external environment and provides the input air sample to the sensor array, and at least one valve to provide exhaust air out to the external environment, in an open-loop flow operation of the sensor system in which the sensor array can detect and identify chemicals or contaminants in air samples.

It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments and, together with the description, serve to explain the principles of the invention.

DETAILED DESCRIPTION

Reference will now be made in detail to embodiments, examples of which are illustrated in the accompanying drawings. An effort has been made to use the same reference numbers throughout the drawings to refer to the same or like parts.

Unless explicitly stated otherwise, "and" can mean "or," and "or" can mean "and." For example, if a feature is described as having A, B, or C, the feature can have A, B, and C, or any combination of A, B, and C. Similarly, if a feature is described as having A, B, and C, the feature can have only one or two of A, B, or C.

Unless explicitly stated otherwise, "a" and "an" can mean "one or more than one." For example, if a device is described as having a feature X, the device may have one or more of feature X.

The inventor of this application has determined that providing a suitable adsorption package and suitable flow circulation will enhance the detection capability and improve robustness sensor systems. Furthermore, a portable sensor unit can still be obtained with addition of a suitable adsorption package as described herein below.

A first embodiment is directed to an improved sensor unit, whereby that improved sensor unit is referred to herein below as Electronic Nose with Close-Loop-Adsorption Circulation, or ENCLAC.

Figure 1:
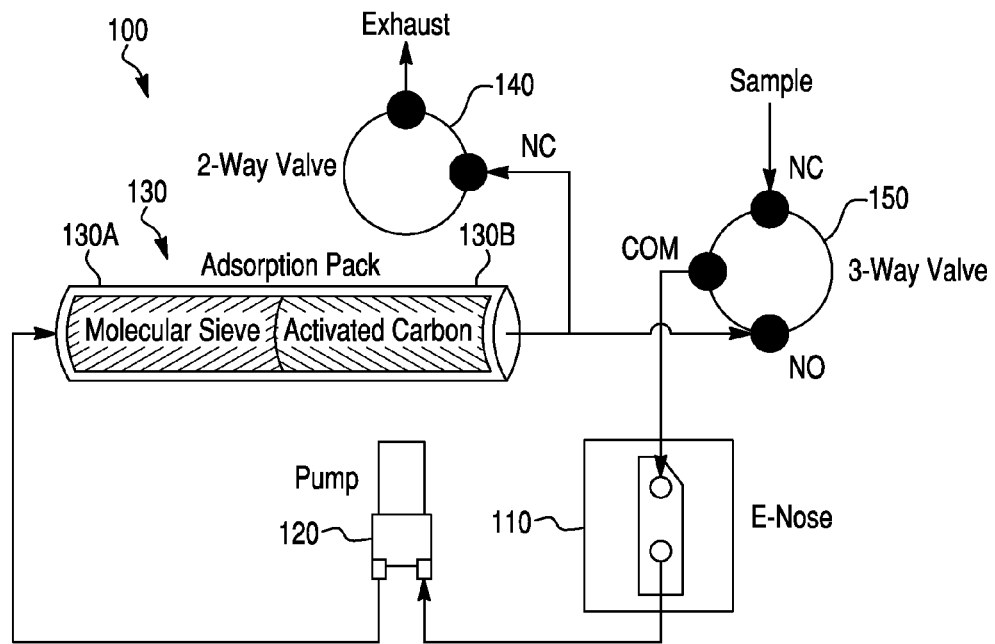
FIG. 1 is a flow diagram showing a close-loop adsorption circulation sensor unit according to a first embodiment.

FIG. 1 is a flow diagram of the ENCLAC sensor unit 100, in accordance with a first embodiment. The ENCLAC sensor unit 100 includes an electronic nose unit 110 that senses sample air, processes data corresponding to the sensed sample air, and makes an identification based on the processed data. The electronic nose unit 110 can be the same as the electronic nose unit utilized in the ENOSE® sensor unit, whereby the electronic nose unit 110 includes a sensor array (not shown) for sampling an environment (e.g., air, gas or liquid, or solid), a processor (not shown) for processing data corresponding to the sampled environment, and an identification unit (not shown) configured to identify the processed data based on particular algorithms. By way of example and not by way of limitation, Adaptive Differential Ratio-metric Detector, using one or more pairs of differential sensors (e.g., carbon nanotube or polymer composite sensors) in a sensor array, can be utilized to categorize and thereby identify an unknown sample, such as, for example, an environmental sample.

The ENCLAC sensor unit 100 according to the first embodiment also can include a diaphragm pump 120 that receives an output from the electronic nose unit 110 and that drives air flow through the system making up the ENCLAC sensor unit 100.

The ENCLAC sensor unit 100 according to the first embodiment further includes an adsorption package 130 that receives the driven air flow from the diaphragm pump 120, and that traps moisture and chemical gas or vapors, so that the electronic nose unit 110 will have a substantially clean and substantially dry purge air, and hence a steady and repeatable baseline. In the first embodiment, the adsorption package 130 includes a molecular sieve 130A as a first portion and activated carbon 130B as a second portion.

The ENCLAC sensor unit 100 according to the first embodiment also can include a 2-way solenoid valve 140 and a 3-way solenoid valve 150, which are both connected to the activated carbon portion 130B of the diaphragm pump 130. The 2-way solenoid valve 140 and the 3-way solenoid valve 150 are programmed to guide the flow direction of the ENCLAC sensor unit 100, to be described in detail below. Valves other than solenoid valves can be utilized in the present invention, such as electrical or mechanical valves.

The operation of the ENCLAC sensor unit 100 can be described as operating in two stages. When the ENCLAC sensor unit 100 runs, it goes through the two stages alternately, whereby it starts with a purge stage and then it goes into a sample stage, and so on; e.g., purge-sample-purge-sample-purge.

Figure 2:
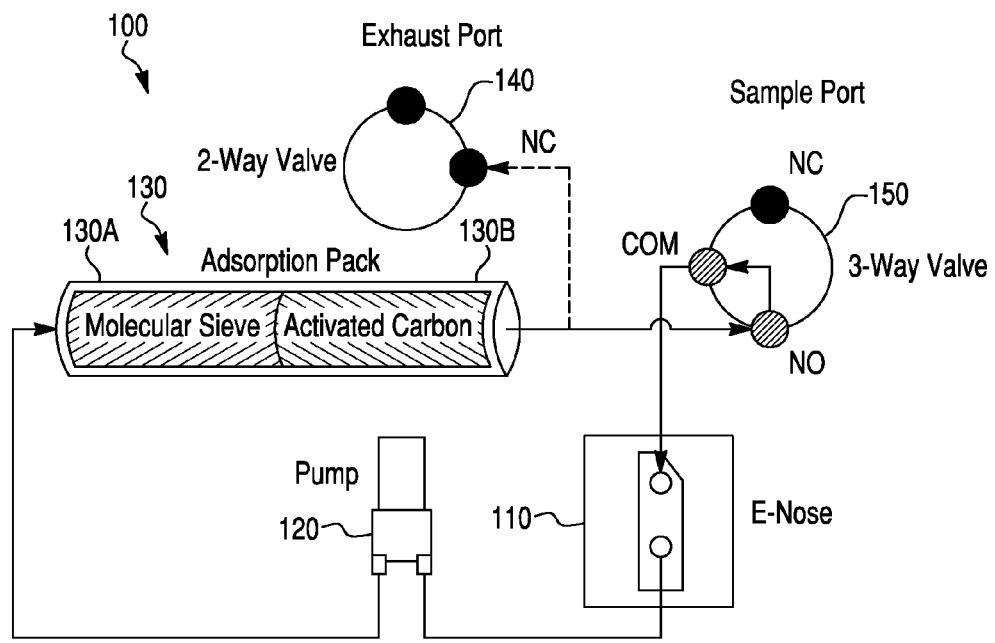
FIG. 2 is a flow diagram showing a purge stage of the sensor unit according to the first embodiment.

In the purge stage, also referred to as "idle stage," as illustrated in FIG. 2, both the 2-way solenoid valve 140 and the 3-way solenoid valve 150 are not actuated, whereby the exhaust port of the 2-way solenoid valve 140 and the sample port of the 3-way solenoid valve 150 are closed. The air flow of the ENCLAC sensor unit 100 is pumped by the diaphragm pump 120, and it runs a closed-loop circulation in the purge stage. The air left in the system is pumped by the diaphragm pump 120 through the adsorption package 130, whereby moisture and trace chemicals can be adsorbed by adsorption materials in the molecular sieve portion 130A and the activated carbon portion 130B. The molecular sieve 130A portion can be any suitable molecular sieve, such as, for example, 4A, 3A, A and 13X molecular sieve. In one embodiment, the molecular sieve can be a 4A molecular sieve. The air stream that has passed through the adsorption package 130 is substantially dry and substantially clean, and will then enter a normal-open (NO) port of the 3-way solenoid valve 150 and exit the 3-way solenoid valve 150 via its common port (COM). The air stream that has passed out of the 3-way solenoid valve 150 via its common port (COM) then enters the electronic nose 110, and then through the electronic nose 110 to the diaphragm pump 120, making it a close-loop circulation. That is, air does not enter the ENCLAC sensor unit 100 and air does not leave the ENCLAC sensor unit 100 during the close-loop circulation.

During the purge stage (or purge period), the sensors (not shown) of the electronic nose unit 110 contact the dry and clean air in the close-loop circulation. The chemicals and moisture previously adsorbed in the sensor films can diffuse out as a result of this contact with the dry and clean air, to be carried by the purge air and then trapped by the adsorption package 130. After the process of desorption reaches equilibrium, the signals of the sensors making up the electronic nose unit 110 will show a low and steady baseline. A monitor unit (not shown) can be utilized to monitor the baseline detection characteristics of the sensors making up the sensor array of the electronic nose unit 110, whereby once the baseline detection characteristics show a low and steady baseline (e.g., beneath a threshold level and within a predetermined high and low range with respect to any two of the sensors), the purge stage can be ended.

Cleaning the sensors increases sensor sensitivity. Accordingly, the use of a close-loop-adsorption circulation will improve the detection characteristics of a sensor system, such as, for example, the ENOSE® sensor system. In one embodiment, the purge period is run for a period of time that is three times as long as the (preceding and next) sample stage is run, to assure a clean sensor array.

Figure 3:
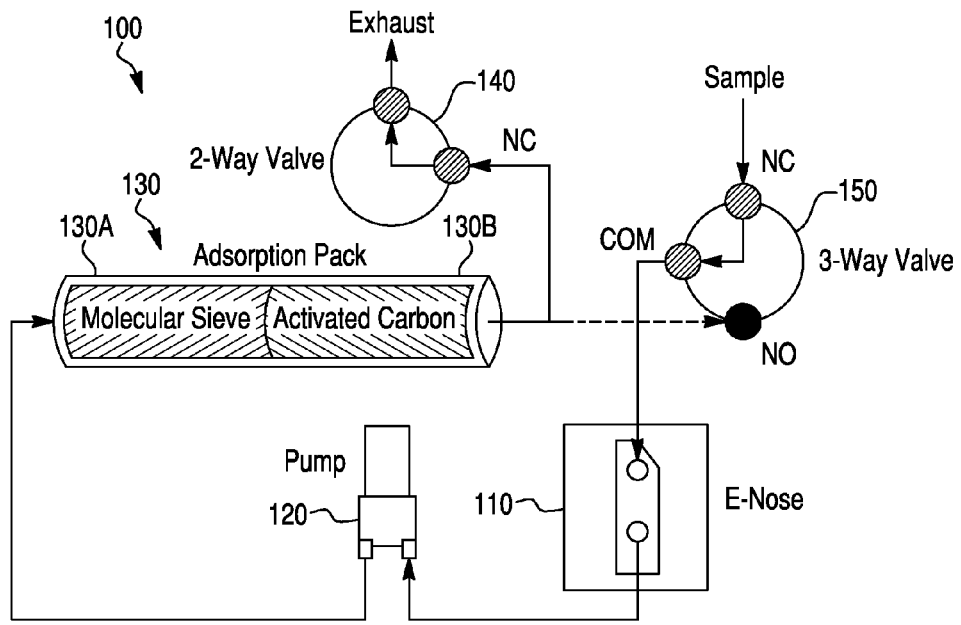
FIG. 3 is a flow diagram showing a sample stage of the sensor unit according to the first embodiment.

During the sample stage (or sample period), as shown in FIG. 3, both the 2-way solenoid valve 140 and the 3-way solenoid valve 150 are actuated by a control signal (not shown). The 3-way solenoid valve 150 opens to the sample port to receive an air sample, and the 2-way solenoid valve 140 opens to an exhaust port to exhaust air from the system. An air sample is introduced, passes through the normal-close (NC) port of the 3-way solenoid valve 150, then through the common port (COM) of the 3-way solenoid valve 150, then through the electronic nose unit 110 (to be detected and classified), and then to the diaphragm pump 120. The air sample can then be pumped by, for example, a diaphragm pump 120 through the adsorption package 130, and then to the normal-close (NC) port of the 2-way solenoid valve 140, which is in the open state), to the exhaust port of the 2-way solenoid valve 140. In one embodiment, the normal-open (NO) port of the 3-way solenoid valve is closed during the sample period, preventing air from being exhausted out of the sample port.

During the sample period, the sensors of the electronic nose unit 110 are contacting the sample air, whereby chemicals and moisture in the sample air will diffuse into sensor films and cause sensing signal changes. These signals are then digitized and processed by a microprocessor (not shown) that runs certain algorithms that are used to categorize the sample air (e.g., the sample air contains X % of ammonia gas and Y % of hydrocarbon gas). The analytical results obtained by the microprocessor can be presented by one or more of an LCD display, alarm lights, and an audio beep, for example.

The sample period can vary depending on flow rate and applications, whereby the higher the flow rate is, the shorter the sample time that is required to detect chemicals or contaminants in the air flow. For example, when the ENCLAC sensor unit 100 is running at a flow rate of 150 ml/min, it will take approximately 3 seconds to detect low concentration of ammonia gas or hydrocarbon vapors.

Figure 4:
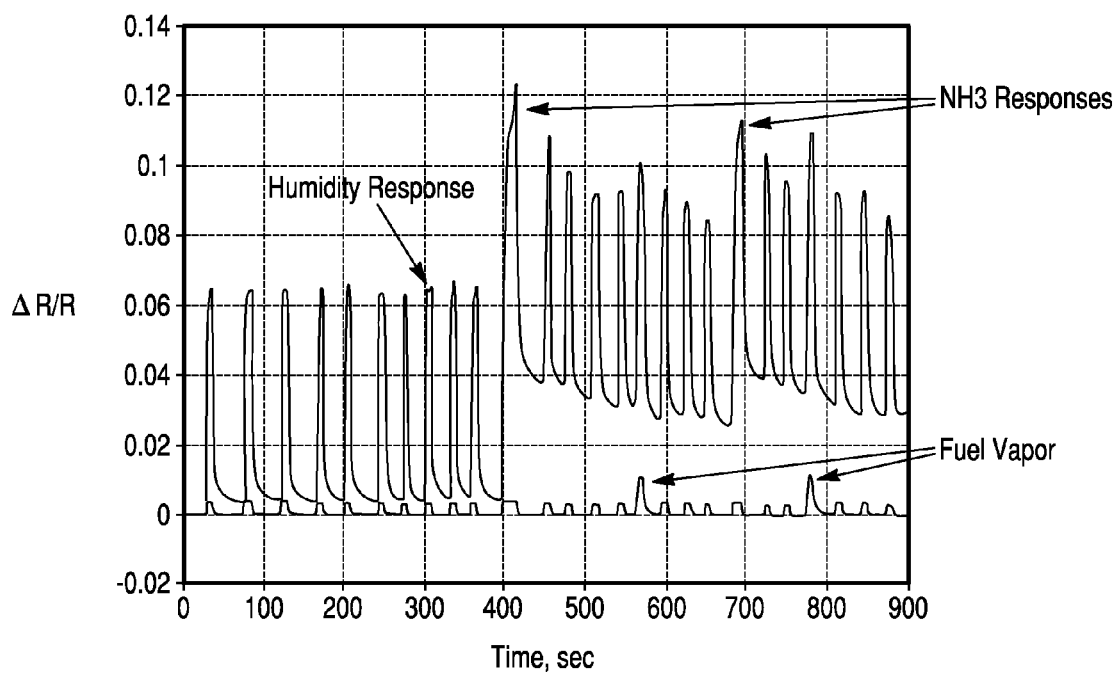
FIG. 4 is a plot showing response characteristics of the sensor unit according to the first embodiment.

The sensors making up the ENCLAC sensor unit 100 are constructed by choosing sensors or sensor technologies based on orthogonal characteristics of sensor interactions to detect analytes, whereby other types of sensors or sensor technologies can be utilized, while remaining within the spirit and scope of the invention. FIG. 4 is a plot showing that the sensors of the ENCLAC sensor unit 100 respond to water vapor, 30 ppm (parts per million) ammonia gas, and low concentration diesel vapor. In this case, the responses increase when the ENCLAC sensor unit 100 is sampling, and the responses decrease when the ENCLAC sensor unit 100 is purging. One sample/purge cycle will generate one peak per each sensor element on the plot. The differences among ammonia ($NH_3$), diesel (fuel vapor) and humidity samples can be seen clearly in FIG. 4. Using a powerful algorithm such as the Adaptive Differential Ratio-Metric Detector (ADRD) algorithm, these chemicals can be easily detected and identified.

In summary, the ENCLAC sensor unit 100 has close-loop-adsorption circulation for an electronic nose unit 110, an adsorption package 130, and a close-loop circulation flow path, whereby a diaphragm pump 120 provides for air flow within the close-loop circulation flow path. Having the adsorption package 130 provided in the circulation loop, in which the adsorption package 130 contains a molecular sieve and activated carbon, causes moisture in the air flow to be trapped and also chemicals in the air flow to be trapped. The purge air having passed through the adsorption package 130 is substantially clean and substantially dry, which provides the sensors with a steady signal baseline, which is a desirable feature.

During a purge or idle stage (or period), the diaphragm pump 120 makes a close-loop circulation with a constant flow rate. The circulated air is made substantially clean and substantially dry by having passed through the adsorption package 130, whereby outside moisture will get into the system. Typically, only during a sample stage (or period) will the ENCLAC sensor unit 100 input a sample flow from the outside environment and exhaust air to the outside environment. Therefore, the close-loop circulation enhances the usable lifetime of the adsorption package 130. The present invention according to the first embodiment provides for substantially clean and substantially dry air by way of the purge stage. By way example and not by way of limitation, a substantially clean and dry air flow may correspond to an air flow that has less than 2 ppm of chemical vapor and that has a humidity of less than 2% RH at ambient temperature. By way of another example, a substantially clean and dry air flow may correspond to an air flow that has less than 5 ppm of chemical vapor and that has a humidity of less than 5% RH at ambient temperature.

Still further, the ENCLAC sensor unit 100 can be made portable or even handheld, since it does not require clean and dry air from an outside source, such as a purified compressed air or zero air from air cylinders that would have been required if close-loop circulation according to the first embodiment was not utilized.

Also, the ENCLAC sensor unit 100 is less susceptible to an external source of air contamination, and hence this will extend the life of the ENCLAC sensor unit 100 beyond that of non-close-loop systems.

The sensor making up the electronic nose unit 110 can be single-wall-carbon-nanotube (SWNT) sensors and polymer composite sensors, in one possible implementation, whereby the electronic nose unit 110 has powerful microprocessor and detection/classification algorithms to process sensing signals in one possible implementation.

In a handheld or portable implementation of the electronic nose unit 110, a push button provided on the handheld or portable unit initiates a sample taking, when actuated by a user. In another possible implementation, the ENCLAC sensor unit 100 is programmed to initiate samples in sequence and in a timely manner, without requiring user actuation of a push button. Since the samples are initiated either manually or by program, synchronization signals can be generated during the sample events. With the synchronization signals, an ADRD algorithm or other static multivariate algorithm can be used for classification and identification of sensed signals. Using the ADRD algorithm, which differs from conventional multivariate algorithms, the ENCLAC sensor unit 100 does require training or calibration, resulting in significant cost reduction of time and labor costs.

The ENCLAC sensor unit 100 can be utilized to detect low concentration ammonia gas and hydrocarbon vapors, as well as other types of chemical contaminants by utilizing sensors targeted for detecting those other types of chemical contaminants.

The embodiments described above have been set forth herein for the purpose of illustration. This description, however, should not be deemed to be a limitation on the scope of the invention. Various modifications, adaptations, and alternatives may occur to one skilled in the art without departing from the claimed inventive concept. For example, the types of differential sensors that can be utilized in the present invention include ion-mobility spectrometry (IMS) sensors, metal-oxide semiconductor (MOS) sensors, and photoionization detector (PID) sensors. Other uses of the invention include homeland security applications (e.g., bomb detection), toxic industrial chemical (TIC) detection, and breath analysis (e.g., for use by police to test a vehicle driver suspected of being intoxicated). The spirit and scope of the invention are indicated by the following claims.

What is claimed is:

1. A detection and identification system, comprising:
    a sensor unit that is configured to detect and identify at least one chemical included in an air flow, the sensor unit including a sensor array;
    a pump that is configured to drive the air flow through the detection and identification system, the pump receiving the air flow that has passed out of the sensor unit;
    an adsorption unit that is configured to substantially dry and substantially clean the air flow within the detection and identification system, the adsorption unit receiving the air flow that has passed out of the pump; and
    at least one valve that is configured to receive the substantially dry and substantially clean air flow that has passed through the adsorption unit,
    wherein the at least one valve provides the substantially dry and substantially clean air flow to the sensor unit in a close-loop circulation operation of the detection and identification system to thereby clean the sensor array in a purge stage, and
    wherein the at least one valve operates to receive input air from an external environment and then to the sensor array, and the at least one sensor operates to provide exhaust air out to the external environment, in an open-loop flow operation of the detection and identification system in which a chemical or contaminant in the sample is detected and identified in a sample stage.

2. The system according to claim 1, wherein the sensor array includes at least two differential sensors that are orthogonal sensors with respect to detection of at least one analyte.

3. The system according to claim 2, wherein the at least two differential sensors includes a first sensor that corresponds to a carbon nanotube sensor and a second sensor that corresponds to a polymer composite sensor.

4. The system according to claim 1, wherein the pump is a diaphragm pump.

5. The system according to claim 1, wherein the adsorption unit comprises:
   a molecular sieve portion; and
   an activated carbon portion.

6. The system according to claim 1, wherein the at least one valve comprises:
   a two-way valve that includes an exhaust port and a normal-close port; and
   a three-way value that includes a normal-close port, a normal-open port, and a common port.

7. A non-transitory computer readable medium storing a computer program, which, when executed on a computer or a microprocessor, is used to control operation of a sensor system that detects and identifies sensor data, the computer program, when executed on the computer or the microprocessor, performing the steps of:
   detect and identify at least one chemical included in an air flow of the sensor system, the sensor system including a sensor array;
   drive the air flow through the detection and identification system; and
   dry and clean the air flow within the detection and identification system, to thereby provide a substantially clean and substantially dry air flow,
   wherein the substantially dry and substantially clean air flow passes through in a close-loop circulation operation of the sensor system to thereby clean a sensor array of the sensor system during a purge stage, and
   wherein an external air sample passes through the sensor array of the detection and identification system in an open-loop flow operation of the sensor system, to thereby detect and analyze chemicals or contaminants within the external air sample during a detection stage.

8. The non-transitory computer readable medium according to claim 7, wherein the sensor array includes at least two differential sensors that are orthogonal sensors with respect to detection of at least one analyte.

9. The non-transitory computer readable medium according to claim 8, wherein the at least two differential sensors includes a first sensor that corresponds to a carbon nanotube sensor and a second sensor that corresponds to a polymer composite sensor.

10. The non-transitory computer readable medium according to claim 7, wherein the air flow is driven by a diaphragm pump in a controlled way.

11. The non-transitory computer readable medium according to claim 7, wherein the dry and clean step comprises:
   providing the air flow through a molecular sieve portion of an adsorption unit; and
   providing the air flow through an activated carbon portion of the adsorption unit.

12. A method of controlling operation of a sensor system that detects and identifies sensor data, the method comprising the steps of:
   detecting and identifying at least one chemical included in an air flow of the sensor system, the sensor system including a sensor array;
   driving the air flow through the sensor system; and
   drying and cleaning the air flow within the sensor system, to thereby obtain a substantially dry and substantially clean air flow,
   wherein the substantially dry and substantially clean air flow passes through in a close-loop circulation operation of the sensor system to thereby clean a sensor array of the sensor system during a purge stage, and
   wherein external air passes through the sensor array of the sensor system in an open-loop flow operation of the sensor system, to thereby detect and analyze chemicals or contaminants within the external air sample during a detection and identification stage.

13. The method according to claim 12, wherein the sensor array includes at least two differential sensors that are orthogonal sensors with respect to detection of at least one analyte.

14. The method according to claim 13, wherein the at least two differential sensors includes a first sensor that corresponds to a carbon nanotube sensor and a second sensor that corresponds to a polymer composite sensor.

15. The method according to claim 12, wherein the air flow is driven in the driving step by way of a diaphragm pump.

16. The method according to claim 12, wherein the drying and cleaning step comprises:
   providing the air flow through a molecular sieve portion of an adsorption unit; and
   providing the air flow through an activated carbon portion of the adsorption unit.

* * * * *